United States Patent
Plant et al.

(10) Patent No.: US 9,213,021 B2
(45) Date of Patent: Dec. 15, 2015

(54) SELF-UNLOCKING FLUID-TIGHT CONNECTOR

(75) Inventors: Kenneth R. Plant, Leominster, MA (US); John C. Conidi, Norwood, MA (US)

(73) Assignee: Waters Technologies Corporation, Milford, MA (US)

( * ) Notice: Subject to any disclaimer, the term of this patent is extended or adjusted under 35 U.S.C. 154(b) by 811 days.

(21) Appl. No.: 13/383,610

(22) PCT Filed: Jul. 16, 2010

(86) PCT No.: PCT/US2010/042252
§ 371 (c)(1),
(2), (4) Date: May 3, 2012

(87) PCT Pub. No.: WO2011/009038
PCT Pub. Date: Jan. 20, 2011

(65) Prior Publication Data
US 2012/0205304 A1   Aug. 16, 2012

Related U.S. Application Data

(60) Provisional application No. 61/226,034, filed on Jul. 16, 2009.

(51) Int. Cl.
*B01L 3/00* (2006.01)
*A61M 39/10* (2006.01)
(Continued)

(52) U.S. Cl.
CPC .......... *G01N 30/6026* (2013.01); *A61M 39/12* (2013.01); *B01L 3/565* (2013.01); *G01N 30/6004* (2013.01); *G01N 30/6034* (2013.01); *G01N 30/6039* (2013.01); *A61M 2039/1016* (2013.01); *B01L 2300/0838* (2013.01)

(58) Field of Classification Search
None
See application file for complete search history.

(56) References Cited

U.S. PATENT DOCUMENTS 2,059,920 A    11/1936   Weatherhead, Jr.
4,281,679 A *   8/1981   Stearns ...................... 137/515.5
(Continued)

FOREIGN PATENT DOCUMENTS

WO    WO 2006091952 A1 * 8/2006

OTHER PUBLICATIONS

PCT International Search Report, Form PCT/ISA/210/220, dated Sep. 14, 2010, 5 pages.
(Continued)

*Primary Examiner* — Katherine Zalasky
*Assistant Examiner* — Kara Graber
(74) *Attorney, Agent, or Firm* — Nielsen IP Law LLC (57) ABSTRACT

A connector is used to connect a conduit to a threaded orifice of a fluidic component, such as a component of an apparatus for chromatography. The connector includes a flexible fitting, a deformable fitting, and a compression fitting. The flexible fitting fixes the position of the conduit with respect to the threaded orifice. The deformable fitting provides a fluid-tight seal between the fluidic conduit and the threaded orifice. The compression fitting includes an external-thread portion for attachment to the orifice, to urge the flexible fitting toward an outer surface of the fluidic conduit, and to urge the deformable fitting toward both the outer surface and the orifice, a cam portion in mechanical communication with the flexible fitting via a through-hole in the external thread portion, and a graspable portion in rotatable communication with the cam portion.

12 Claims, 7 Drawing Sheets

(51) Int. Cl.
*G01N 30/60* (2006.01)
*A61M 39/12* (2006.01)
*B01D 15/00* (2006.01)

(56) References Cited

U.S. PATENT DOCUMENTS

2002/0109353 A1    8/2002  Guest
2005/0197646 A1*   9/2005  Connell et al. ............... 604/533
2006/0113794 A1*   6/2006  Plant et al. ................... 285/339
2008/0309076 A1   12/2008  Cormier
2010/0224543 A1*   9/2010  Ellis et al. .................. 210/198.2
2010/0224546 A1*   9/2010  Ellis et al. .................... 210/232
2012/0192968 A1*   8/2012  Bonnal et al. ............. 137/454.2

OTHER PUBLICATIONS

PCT International Written Report, Form PCT/ISA/210/220, dated Sep. 14, 2010, 7 pages.

* cited by examiner

SELF-UNLOCKING FLUID-TIGHT CONNECTOR

CROSS REFERENCE TO RELATED APPLICATIONS

This application claims benefit of and is a continuation of to U.S. Provisional Application No. 61/226,034, filed Jul. 16, 2009. The contents of these applications are expressly incorporated herein by reference in its entirety.

TECHNICAL FIELD

The invention generally relates to connectors, and, more particularly, to high-pressure connectors for use in chromatography systems.

BACKGROUND INFORMATION

Gas and liquid chromatography are processes used in analytical and preparative chemistry. Typically, a stationary porous material is held in a vessel, such as a column, while a sample compound in a carrier fluid passes through the porous material. In some cases, the stationary material is an inert powder coated with a stationary liquid agent.

Various distinct chemical compounds contained in a carrier fluid can have varying affinities for a stationary phase. Consequently, as the mobile fluid moves through a chromatographic column, various chemical compounds are delayed by varying times due to their interaction with the stationary phase. These various compounds emerge from the column at different times and are detected individually by, for example, a refractometer, an ultra-violet light detector or some other analytical apparatus in which the fluid flows upon leaving the chromatographic column.

Much of the effort in the development of chromatography apparatus and techniques seeks to idealize the distribution and flow of a mobile phase through a porous stationary phase. Some work has been directed to the design of end fittings to connect components through which a fluid flows. Such connectors generally should be leak resistant and mechanically stable, and should optimize the initial distribution of a mobile liquid at the top of a column.

Problems associated with the design and use of connecting components are particularly difficult in high-pressure chromatography. Pressures in the range of, for example, 1,000 to 5,000 psi or higher can be used in liquid chromatography. Consequently, dependable sealing techniques should be used. Problems arise in, for example, assuring an adequate seal without excessive wear of deformed metal parts. For example, some fittings have ferrules which are tightened about a tube. After use, the shape of a tube or column can be distorted by the force exerted on the ferrule during tightening of end fittings.

One approach to making a high-pressure connection utilizes a connector that includes a compression screw and ferrule. In such a device, the liquid seal between a tube and another component is achieved by compressing the ferrule against both an orifice of the component and the tube to both seal and stabilize the tube. Maintenance of a desired position of a tube can be desirable to eliminate "dead volume" between the end of the tube and the component, and to avoid pressing the tube axially against the orifice with an undesirable force.

SUMMARY OF THE INVENTION

The invention arises, in part, from the realization that one can decouple sealing and stabilizing forces involved in connections between fluid-carrying components, such as two tubes or a tube and a vessel. By decoupling these forces, improved control can be obtained over a fluid-tight seal between components, and over the mechanical stability of the connected components. Decoupling is optionally achieved through use of a connect that includes a compression screw, a collet and a ferrule, for example. The invention also arises, in part, from the realization that a conventional compression screw is advantageously modified to include a cam portion that acts to release a forward threaded portion from other portions of a connector, such as from a collet.

Thus, some embodiments of a connecting device include a ferrule to provide a seal between a conduit and a fluidic component, a collet to secure the conduit relative to the fluidic component, and one or more members that apply mechanical forces to the ferrule and the collet. In some embodiments, a collet secures an outer axial surface of the conduit without pressing the conduit toward the fluidic component.

Accordingly, one embodiment of the invention features a device for connecting a fluid conduit to an orifice of a fluidic component. The device includes a flexible fitting, a deformable fitting, and a compression fitting. The flexible fitting fixes the position of the conduit with respect to the threaded orifice. The deformable fitting provides a fluid-tight seal between the fluidic conduit and the threaded orifice. The compression fitting includes an external-thread portion for attachment to the orifice, to urge the flexible fitting toward an outer surface of the fluidic conduit, and to urge the deformable fitting toward both the outer surface and the orifice, a cam portion in mechanical communication with the flexible fitting via a through-hole in the external-thread portion, and a graspable portion in rotatable communication with the cam portion. During removal of the connector from the orifice, the cam portion assists release of the flexible fitting from the compression fitting.

When the graspable portion is rotated in a lock direction, such as clockwise, the graspable portion urges the cam portion axially away from the flexible fitting until the cam portion encounters a stop. While pressing against the stop, the cam portion also urges the external-thread portion to rotate to secure the external-thread portion to the orifice. When the graspable portion is rotated in a release direction, such as counterclockwise, the graspable portion urges the cam portion axially toward the flexible fitting until the cam portion engages in mechanical communication with the flexible fitting. At this point, the cam portion urges the flexible fitting axially toward the orifice; at the same time, the graspable portion urges the cam portion to rotate in the release direction, which urges the external-thread portion to rotate to release the external-thread portion from the orifice. Thus, the external-thread portion and the flexible fitting are urged away from each other; the flexible fitting tends to be held in place while the external-thread portion tends to back off from the orifice while being unscrewed from the orifice.

A second embodiment of the invention features a liquid-chromatography apparatus. The apparatus includes a conduit, a fluidic component having a threaded orifice; and a connector connecting the conduit to the threaded orifice of the fluidic component. The connector includes a flexible fitting, a deformable fitting, and a compression fitting. The compression fitting includes an external-thread portion for attachment to the orifice, a cam portion in mechanical communication with the flexible fitting via a through-hole in the external-thread portion, and a graspable portion in rotatable communication with the cam portion. The external-thread portion, when attached to the threaded orifice, urges the flexible fitting toward the outer surface of the conduit, and urges the deformable fitting toward both the outer surface and the orifice.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1b is a three-dimensional illustration of the connector of FIG. 1a;

FIG. 1c is a cross-sectional view of the connector of FIG. 1a;

FIG. 2a is a three-dimensional view of a collet, associated with the connector of FIG. 1a;

FIG. 2b is an end view of the collet of FIG. 2a;

FIG. 2c is a longitudinal cross-sectional view of the collet of FIG. 2a;

FIG. 3b is a three-dimensional exploded view of the connecting device of FIG. 3a; and FIG. 3c is a three-dimensional exploded view of threaded portions of the device of FIG. 3a.

DETAILED DESCRIPTION

Figure 1A:
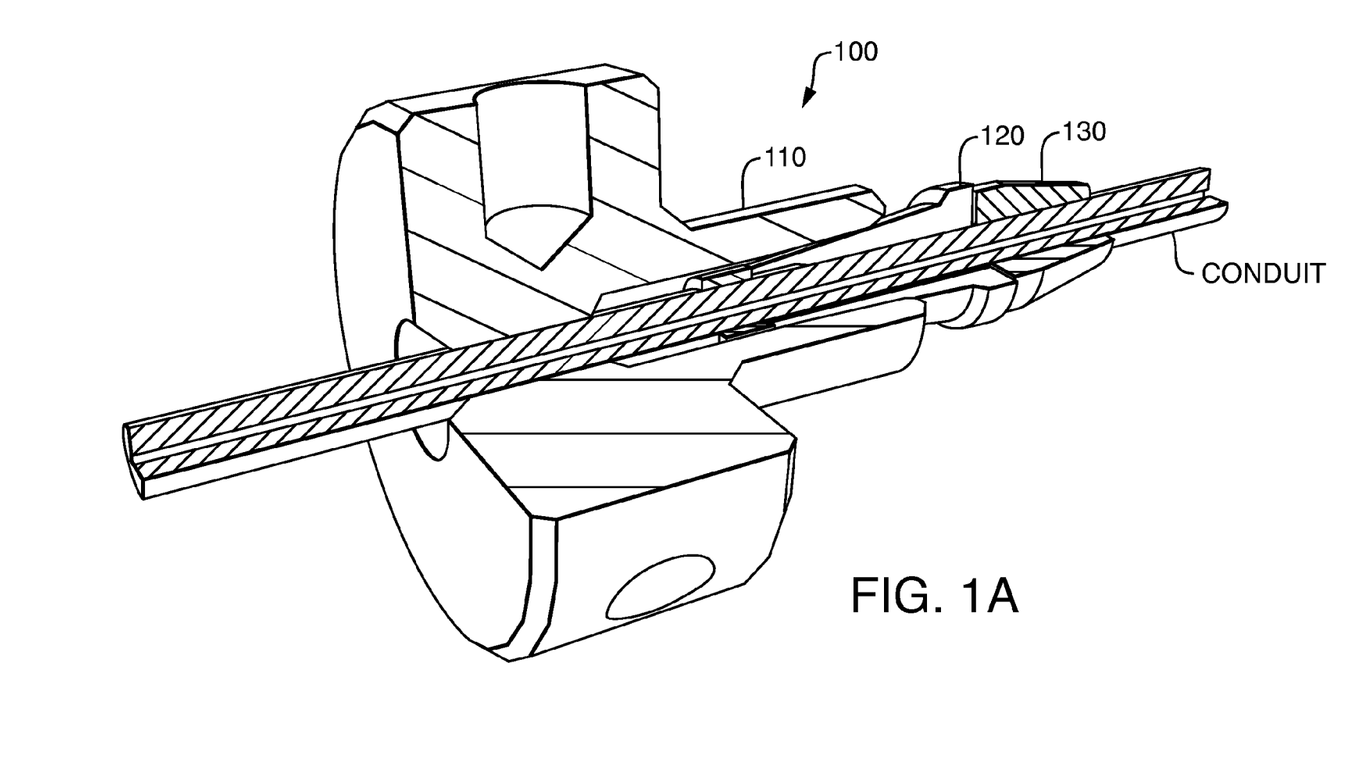
FIG. 1a is a cutaway diagram illustrating a connector.

FIG. 1a is a cutaway three-dimensional diagram illustrating a connecting device 100, in accordance with one embodiment. The device 100 includes a compression fitting 110, a flexible fitting 120, and a deformable fitting 130. The device 100 is used to connect components that support the flow of a fluid, such as a liquid or gas. The fluid can include a mixture of material. The device 100 can be used, for example, to connect a conduit, such as a tube, to a vessel, such as a column, in an analytical instrument. The instrument is, for example, a chromatographic system.

For convenience of description, the flexible fitting 120 will be referred to herein as a "collet" and the deformable fitting will be referred to herein as a "ferrule". It should be understood, however, that use of these terms is not intended to limit embodiments of the invention to devices that include collet(s) and/or ferrule(s). Moreover, although the embodiments described herein include fittings that completely surround a conduit and have portions that form a continuous ring disposed around a conduit, some alternative embodiments include fittings that partially surround a conduit and/or only surround a conduit with a discontinuous ring.

The components 110, 120, 130 of the device 100 are configured so that the compression fitting 110 compresses a portion of the collet 120 against an axially aligned outer surface of the tube, and simultaneously compresses the ferrule 130 against the tube and the vessel. The compression fitting 110 applies a force to the ferrule 130 via the collet 120 acting as in intermediary.

The components 110, 120, 130 are fabricated from any suitable materials. For example the ferrule 130 includes any suitably deformable material, such as a polymer, including suitable polymers known to one having ordinary skill in the chromatographic arts. The collet 120 includes any suitably flexible material, such as a hard polymer and/or a metal, such as a steel. The compression fitting 110 is formed of material(s) suitable for, for example, compression screws, as known to one having ordinary skill, or other suitable materials. Some suitable materials include metals, such as steel or other alloys, polymers, and/or ceramic materials. The components optionally include, for example, mixtures and/or composites and/or layers of materials, with or without coatings.

The ferrule 130 provides a seal between the tube and the vessel, to prevent fluid leakage up to suitably high pressures. By finger tightening the compression fitting, with a torque of, for example, about 50 to about 80 inch-ounces, a leak resistance of about 15 kpsi to 20 kpsi is obtainable.

The ferrule 130 can be sealed with a force of, for example, 20 lbs. According to some principles of the invention, additional force need not be applied to the ferrule to secure the position of the tube. Thus, damage to the device 100, the tube, and/or the vessel can be avoided, and the device can be repeatedly used and disassembled.

Unlike the action of ferrules in some existing connectors, the ferrule 130 need not secure the position of the tube relative to the vessel. For this purpose, the collet 120 secures the position of the tube via the holding force applied with pressure derived from the compression fitting 110. The collet 120, in turn, is indirectly attached to the vessel via a direct contact made by the compression fitting 110.

Figure 1B:
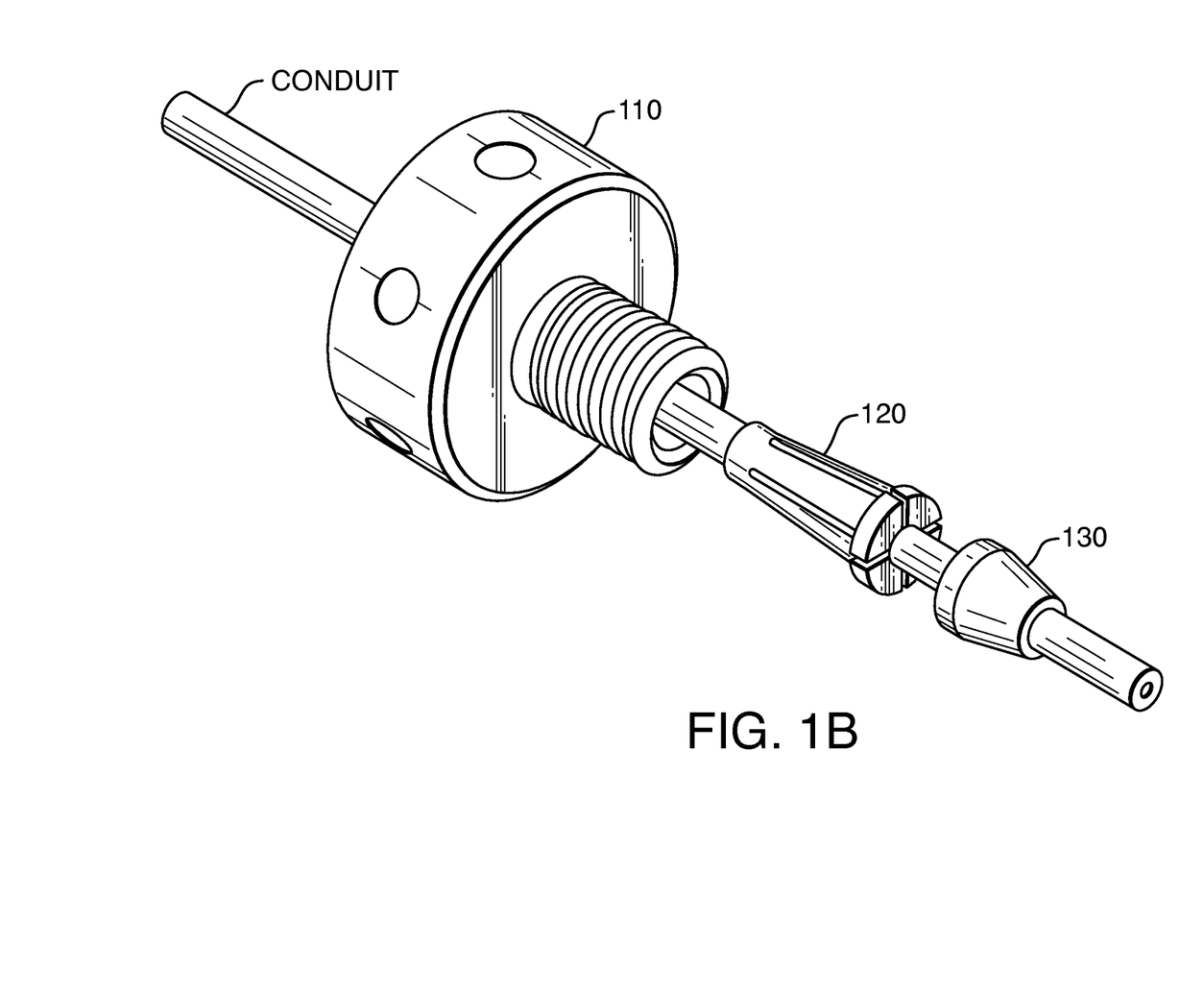

FIG. 1b is a three-dimensional view of the device 100, with the components 110, 120, 130 shown prior to assembly (or after disassembly.) The components 110, 120, 130, in this illustration, are positioned on a conduit, or tube, prior to connecting the conduit to a fitting of, for example, a vessel (or after disconnecting the tube from the vessel.)

Figure 1C:
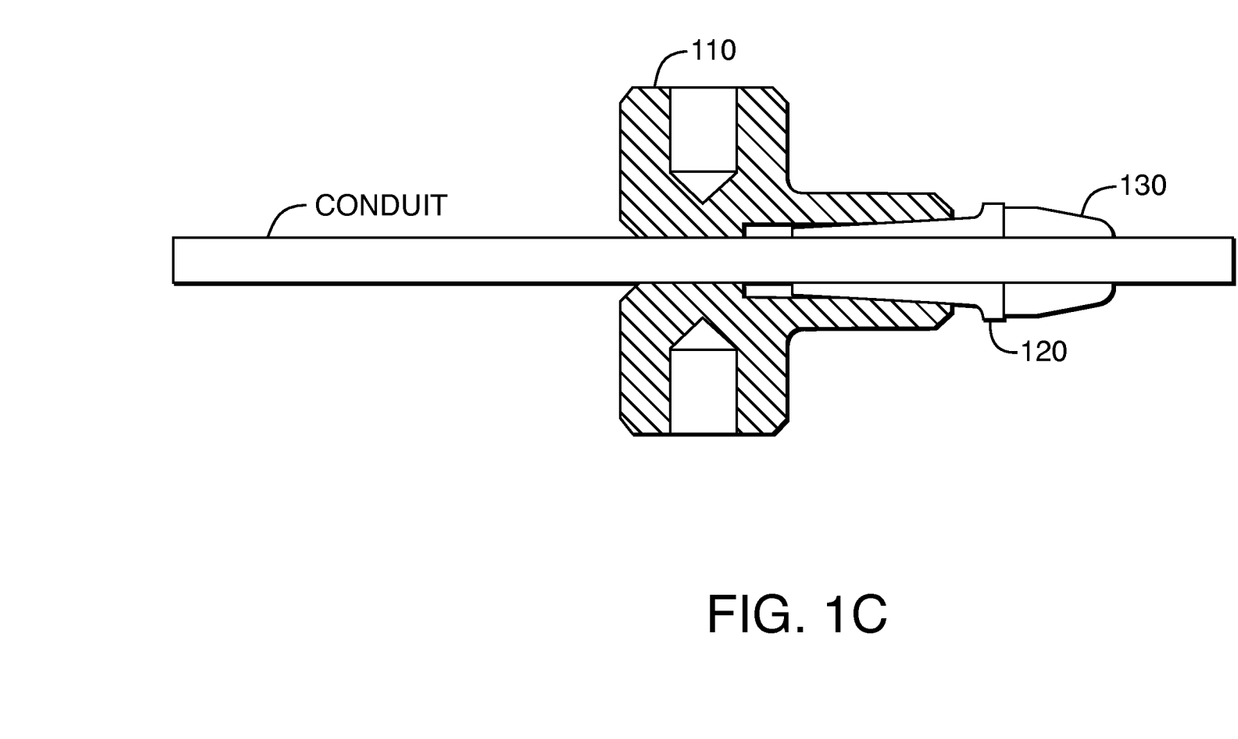

FIG. 1c is a cross-sectional view of the device 100. The components 110, 120, 130 are shown disposed on a conduit and ready for attachment to a fitting.

Figure 2A:
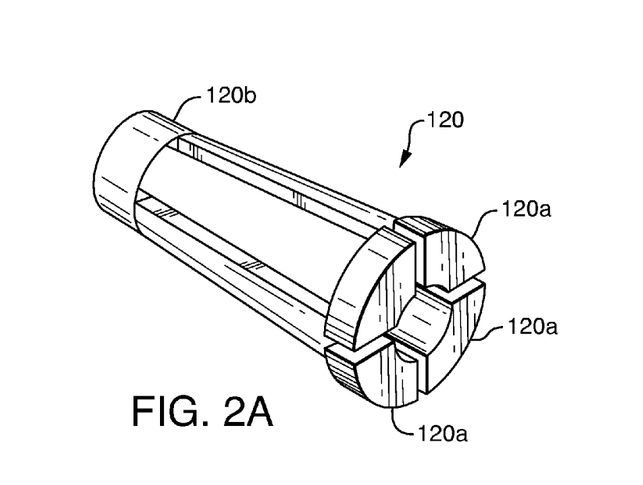
Figure 2B:
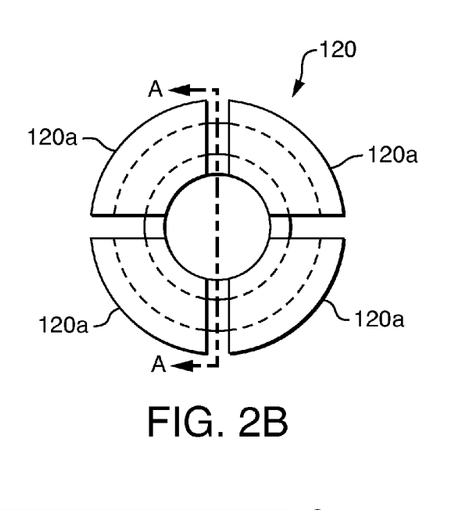
Figure 2C:
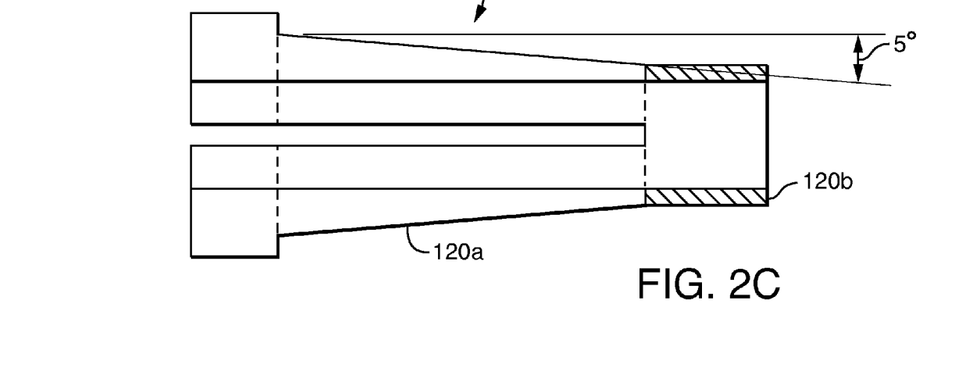

Referring next to FIGS. 2a, 2b, 2c, portions of the device 100 are described in more detail. FIG. 2a is a three-dimensional view of the collet 120, FIG. 2b is an end view of the collet 120, and FIG. 2c is a longitudinal cross-section of the collet 120 through section "A" as indicated in FIG. 2b. The collet 120 includes four fingers 120a and a band 120b from which the fingers 120a extend in a longitudinal (axial) direction. The fingers 120a have a tapered outer surface, which, as described below, are configured to mate with an inner surface of the compression fitting 110.

It will be apparent, in view of the description herein, that alternative embodiments of the invention can include collets having fewer or more than four fingers, or alternative configurations that provide sufficient flexibility to permit pressing the collet against a tube.

The compression fitting 110 has a threaded portion, and a knurled portion to assist finger tightening the threaded portion into a threaded orifice of a vessel. The threaded portion of the compression fitting 110 has an inner surface for receiving and applying a force on the collet 120. The threaded portion has threads on an outer surface, which are configured to mate with threads on an inner surface of the orifice of the vessel.

The inner surface of the compression fitting 110 has a tapered section, which permits gradual application of a force to the fingers 120a of the collet 120 as the compression fitting 110 is threaded into the orifice of the vessel. A taper angle associated with the tapered portion can be selected to support application of a suitable force on the fingers 120a of the collet 120 while also applying a suitable force, via the collet 120, on the ferrule 130. An example of a suitable taper angle is 5°, as illustrated.

In view of the description herein, it will be apparent that dimensions and angles can be selected to provide a desired securing force on a collet 120 and a desired sealing force on a ferrule 130. Dimensions can be chosen, at least in part, for example, to accommodate dimensions of a tube and a vessel orifice. For example, the fitting 110 and collet 120 can each define an interior passageway (a through hole) for insertion of a tube.

A narrowest diameter of a passageway can be selected to accommodate an Outer diameter of a tube, which can be, for example, about 0.06 inches. Overall dimensions of the device 100 can be, for example, less than an inch. In addition to other advantages, the device 100 can more readily accommodate reduction of the space consumed by prior art connecting devices.

Figure 3A:
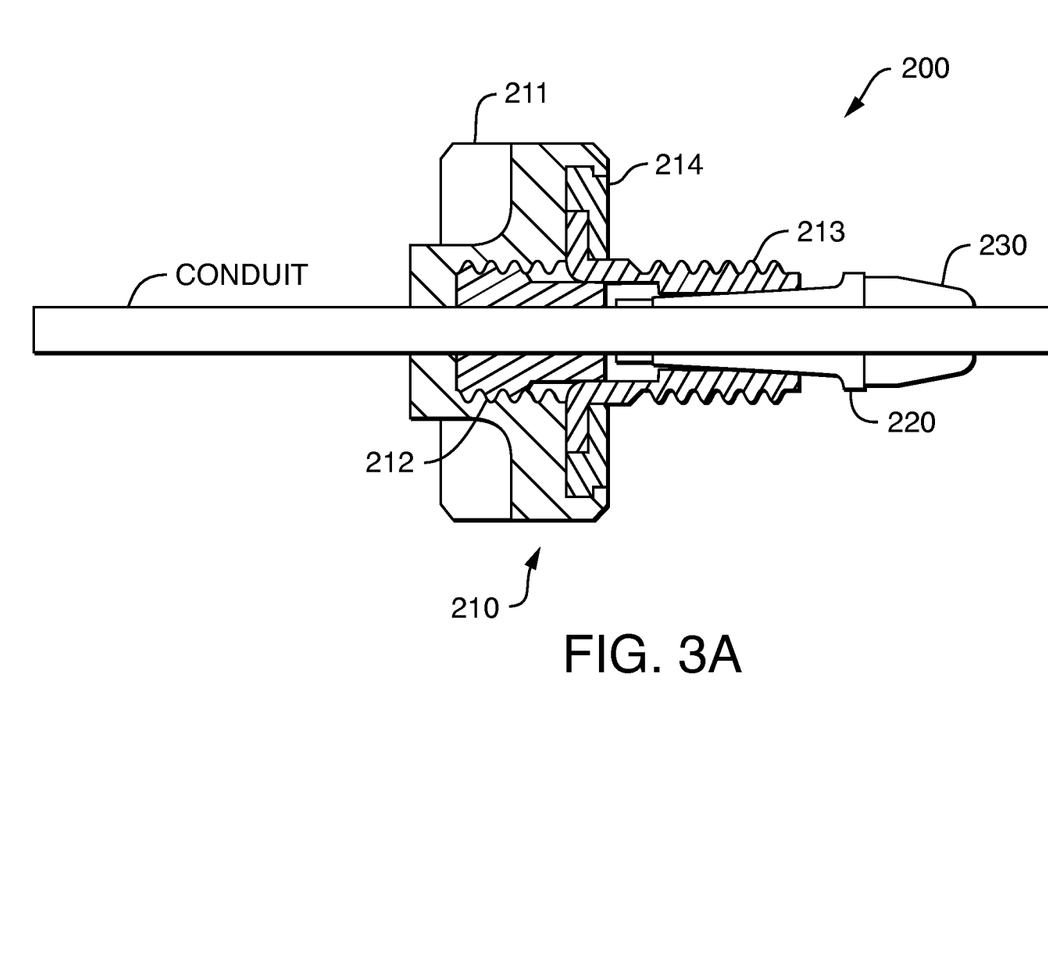
FIG. 3a is a cross-sectional view of a connecting device, in accordance with an embodiment of the invention.
Figure 3B:
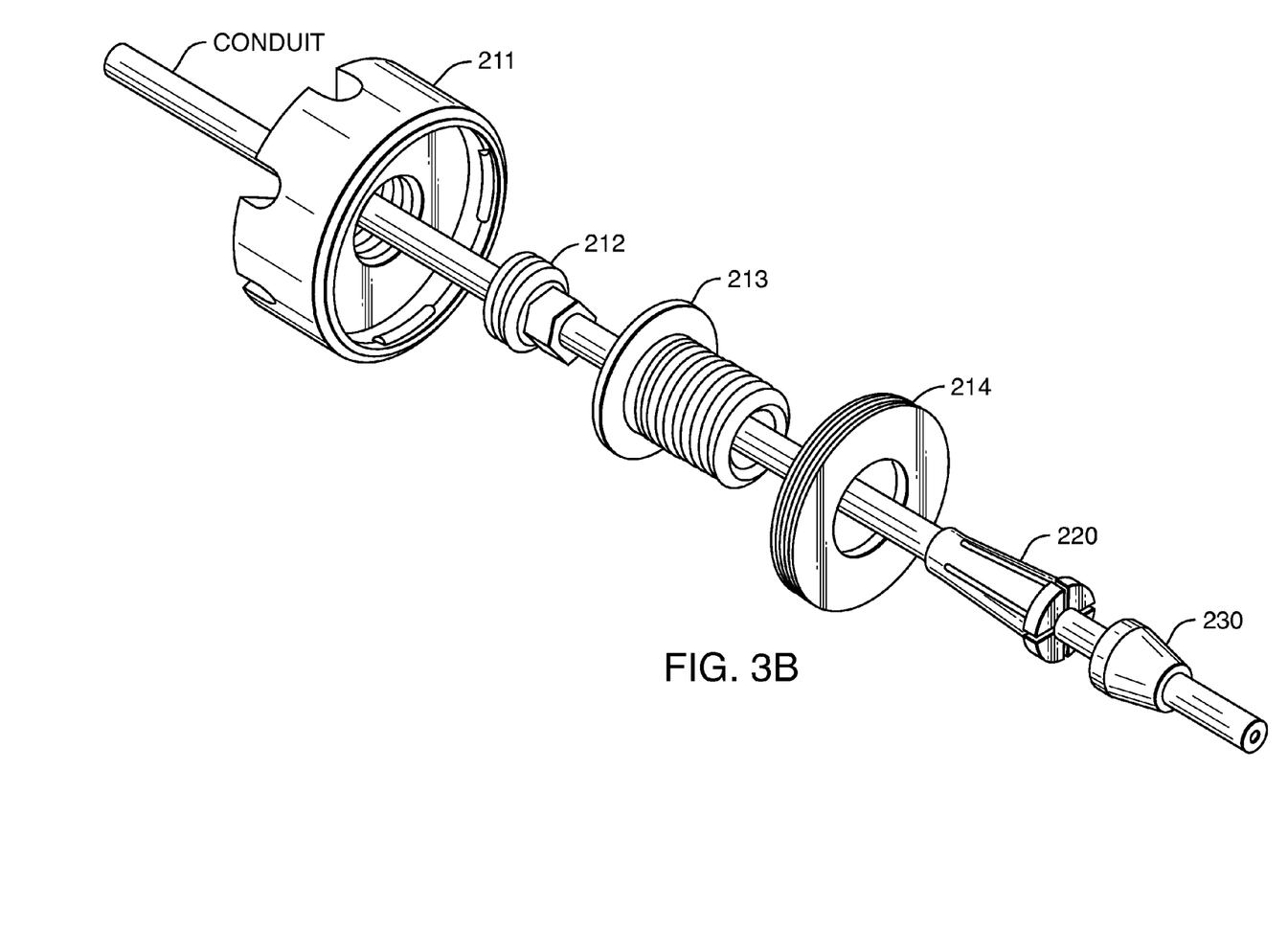

FIG. 3a is a cross-sectional view of an alternative connecting device 200, disposed on a conduit, in accordance with another embodiment of the invention. The device 200 is optionally used to attach, for example, a conduit to an orifice (e.g., a threaded fitting.) FIG. 3b is a three-dimensional exploded view of the connecting device 200. The device 200 includes a compression fitting 210, a flexible fitting 220 (such as the collet 120), and a deformable fitting 230 (such as the ferrule 130.) The device 200 has self-releasing features that—during removal of the device 200—assist separate of the compression fitting 210 and the flexible fitting 220. The flexible fitting 220, for convenience, is also referred to, herein, as a collet; one of skill will recognize, however, that a collet is only one example of a suitable flexible fitting. Similarly, the deformable fitting 230 is also referred to as a ferrule, for convenience.

Figure 3C:
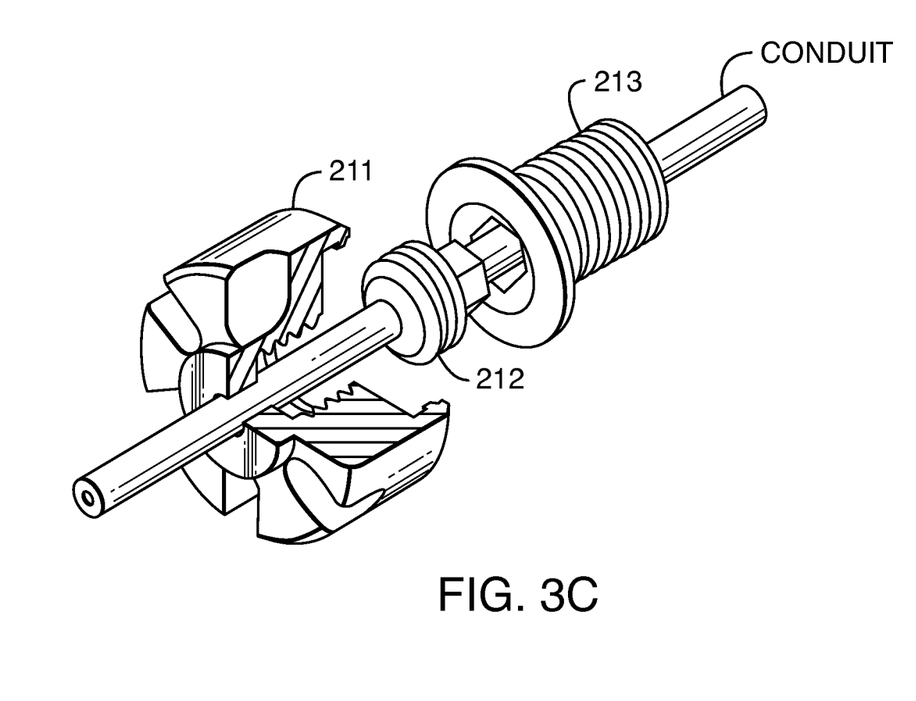

The compression fitting 210 includes a graspable portion 211, a screw-driven cam portion 212, an external-thread portion 213 and a retainer portion 214. The external-thread portion 213 has a thread that mates with an internal threaded surface of a fitting to which the device 200 is to be attached. The screw-driven cam portion 212 has a non-round extension that is disposed in an non-round slot (e.g., an oblong slot) in the external-thread portion 213. A externally threaded rear extension of the cam portion 212 mates with a threaded internal surface of the graspable portion 211. The retainer portion 214 secures the cam portion 212 in the graspable portion 211.

In operation, rotation (preferably clockwise) of the graspable portion 211 causes the cam portion 212 to move rearward within the graspable portion 211 due the cooperative action of the threaded surfaces and the disposition of the extension of the cam portion 212 in the slot of the portion 213. The cam portion 212 generally moves rearward until reaching a limit within a cavity of the graspable portion 211. Further rotation of the graspable portion 211 then causes the cam portion 212 to rotate with the graspable portion 211, which in turn causes the external-thread portion 213 to rotate and tighten with a threaded fitting to which a conduit (or other component) is to be attached. Thus, the tightening and securing action of the device 200 is similar, in some aspects, to the device 100 described above.

To disconnect a conduit (or other component) secured by the device, the graspable portion 211 is rotated in an opposite direction (preferably counterclockwise.) The rotation causes the cam portion 212 to move in a forward direction until the forward extension of the cam portion 212 presses against the collet 220. As the graspable portion 211 continues to apply a rotational force to the cam portion 212, the cam portion 212 continues to apply a forward-directed force to the collet 220; the cam portion 212 now also causes the external-thread portion 213 to rotate in a counterclockwise direction because the cam portion 212 can no longer move in a forward direction due to the constraint of contact with the collet 220.

The external-thread portion 213 unscrews as it rotates, and exits the fitting to which it is attached; at the same time, the collet 220 is loosened from its contact surface with the external-thread portion 213. Thus, the action of the cam portion 212 helps to dislodge a stuck collet 220, if the collet 220 is stuck in the external-thread portion 213, and/or helps to prevent twisting of the conduit by the collet 220, particularly if the collet 220 is stuck in the external-thread portion 213. More generally, the cam portion 212 helps to free the external-thread portion 213 from its frictional contact with the collet 220, whether or not any components are stuck or held together by more than fictional forces.

Thus, more generally, the collet 220 is wedged between the external-thread portion 213 and the conduit. The mating surfaces between the collet 220 and the external-thread portion 213 are preferably configured to provide a desired amount of force at the relevant interfaces. For example, the contact surfaces are preferably angled, and angled to a preferred degree, to achieve a desired force to secure the collet 220. A desired force is generally chosen at least in part in response to a fluidic pressure of operation.

Without the action of the cam portion 212, a release direction rotation of the external-thread portion 213 would tend to cause an undesirable rotation of the conduit, as the wedged collet 220 transmits the rotational force to the conduit.

During this process, the retainer portion 214 helps to retain the cam portion 212 in position in the graspable portion 211. In particular, once there is a selected separation distance between the external-thread portion 213 and the collet 220, the compression fitting 210 may freely be moved away from the collet (and the fitting to which the compression fitting was attached.) Thus, the retainer 214 maintains rotation of the external-thread portion 213 once there is no longer contact between the cam portion 212 and the collet 220.

The retainer portion 214 is attached to the graspable portion 211 via any suitable means. As illustrated, the retainer portion 214 is snap-fitted to the graspable portion 211. In some alternative embodiments a retainer is attached via stakes, a weld or glue. In view of the present description, one of skill will recognize that a variety of configurations are possible for a compression fitting that includes a cam portion, an external-thread portion and a graspable portion, all secured to one another to permit operation of the compression fitting in a manner similar to that described herein.

The self-releasing features of the device 200 provide additional advantages. For example, the device 200 is optionally used in locations in an apparatus that have restricted or difficult access. In contrast, some prior connecting devices require relatively good access to the connecting device after installation. For example, for removal of some prior devices, a component, such as a column, to which the device is connected, must be rotated, for removal, to avoid rotation of a conduit attached to the column via the device.

The self-releasing connecting device 200 has uses in a variety of applications; for example, the device 200 is optionally used to connect tubing to columns and/or fluid stabilizers, and/or for any fluid connection, as in HPLC, to connect, for example, sample loops, solvent mixers, fluidic tees, and/or pump heads, and/or is used in any application involving close proximity of components to be connected or tight routing patterns or limited space. Such devices generally provide a connector that is reusable and permits desired positioning of components to be connected, in a manner that is both mechanically secure and fluidically tight; thus, for example, zero dead volume and minimal axial stress are consistently obtained.

In view of the description provided herein, one of ordinary skill will recognize that the provided examples are merely illustrative and do not limit alternative connector embodiments of the invention to particular illustrated features. For example, the number and/or the configuration of components are optionally varied while still incorporating the key features of the invention. For example, a compression fitting optionally includes a cam portion that is not screw-driven. For example, a cam portion optionally presses indirectly against a collet.

Variations, modifications, and other implementations of what is described herein will occur to those of ordinary skill in the art without departing from the scope of the invention as claimed. Accordingly, the invention is to be defined not by the preceding illustrative description but instead by the scope of the following claims.

What is claimed is:

1. A device for connecting a fluidic conduit to a threaded orifice of a fluidic component, comprising:
    a flexible fitting for substantially fixing a position of the fluidic conduit with respect to the threaded orifice;
    a deformable fitting for providing a substantially fluid-tight seal between the fluidic conduit and the threaded orifice; and
    a compression fitting comprising
        an external-thread portion having a thread and a non-round slot, wherein the thread mates with the threaded orifice and the flexible fitting is wedged between the external-thread portion and the fluidic conduit,
        a screw-driven cam portion having a non-round extension disposed in the non-round slot of the external-thread portion and an externally threaded rear extension,
        a graspable portion having a threaded internal surface, wherein the externally threaded rear extension of the screw-driven cam mates with the graspable portion to secure or loosen the flexible fitting, and
        a retainer portion attached to the graspable portion to retain the screw-driven cam portion in the graspable portion.

2. The device of claim 1, wherein the graspable portion and the screw-driven cam portion secure or loosen the flexible fitting relative to the fluidic conduit.

3. The device of claim 1, wherein the flexible fitting comprises a plurality of flexible fingers defining an axial passage for receiving the fluidic conduit.

4. The device of claim 3, wherein the plurality of flexible fingers define a tapered outer surface.

5. The device of claim 4, wherein the external-threaded portion defines a tapered inner surface that urges the flexible fingers toward a tapered outer surface of the fluidic conduit by applying a pressure to a outer surface of the plurality of flexible fingers.

6. The device of claim 4, wherein a tapered inner surface of the external-threaded portion and the tapered outer surface of the plurality of flexible fingers are threaded.

7. The device of claim 3, wherein the flexible fitting further comprises a band from which the plurality of flexible fingers axially extend, the band defining an axial passage in cooperation with the plurality of flexible fingers.

8. The device of claim 1, wherein the flexible fitting comprises a collet.

9. The device of claim 1, wherein the flexible fitting comprises stainless steel.

10. The device of claim 1, wherein the deformable fitting comprises a ferrule.

11. The device of claim 1, wherein the deformable fitting comprises a polymer.

12. The device of claim 1, wherein the fluidic component comprises a chromatography separation column.

\* \* \* \* \*